US010389532B2

(12) United States Patent
Melrose

(10) Patent No.: US 10,389,532 B2
(45) Date of Patent: Aug. 20, 2019

(54) SECURE MESSAGE ROUTING IN MULTI-TENANT SYSTEM WITHOUT CONTENT INSPECTION

(71) Applicant: YOKOGAWA ELECTRIC CORPORATION, Tokyo (JP)

(72) Inventor: Jeff Melrose, Sugar Land, TX (US)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 196 days.

(21) Appl. No.: 15/713,118

(22) Filed: Sep. 22, 2017

(65) Prior Publication Data

US 2019/0097800 A1    Mar. 28, 2019

(51) Int. Cl.
| H04L 9/30 | (2006.01) |
| H04L 29/06 | (2006.01) |
| G16H 10/60 | (2018.01) |
| G06Q 50/24 | (2012.01) |

(52) U.S. Cl.
CPC ............ H04L 9/30 (2013.01); G16H 10/60 (2018.01); H04L 63/0435 (2013.01); G06Q 50/24 (2013.01)

(58) Field of Classification Search
CPC combination set(s) only.
See application file for complete search history.

(56) References Cited

U.S. PATENT DOCUMENTS

| 2004/0015610 | A1* | 1/2004 | Treadwell | H04L 51/04 |
| | | | | 709/246 |
| 2006/0291422 | A1* | 12/2006 | Rochford | H04L 63/0823 |
| | | | | 370/331 |
| 2009/0083190 | A1* | 3/2009 | Isshiki | G06Q 20/3829 |
| | | | | 705/71 |
| 2010/0241696 | A1* | 9/2010 | Matoba | H04L 67/14 |
| | | | | 709/203 |
| 2014/0181521 | A1* | 6/2014 | Hemphill | H04L 9/0819 |
| | | | | 713/171 |
| 2014/0192766 | A1* | 7/2014 | Akisada | H04W 12/02 |
| | | | | 370/329 |
| 2015/0312758 | A1* | 10/2015 | Redford | H04W 12/04 |
| | | | | 455/410 |
| 2017/0232300 | A1* | 8/2017 | Tran | H04L 67/12 |
| | | | | 434/247 |
| 2018/0167367 | A1* | 6/2018 | John | H04L 63/0428 |
| 2019/0103967 | A1* | 4/2019 | Meng | H04L 9/0637 |

OTHER PUBLICATIONS

Kinsy et al., "Hermes: Secure heterogeneous multicore architecture design", 2017 IEEE International Symposium on Hardware Oriented Security and Trust (HOST), DOI: 10.1109/HST.2017.7951731, May 2017.*

* cited by examiner

*Primary Examiner* — Piotr Poltorak
(74) *Attorney, Agent, or Firm* — Osha Liang LLP

(57) ABSTRACT

A method for message routing in a multi-tenant system includes encrypting an ID of a tenant with a public key that is generated for the tenant together with a corresponding private key; storing a set of the encrypted ID and the public key in both a device and a server of the multi-tenant system; transmitting from the device to the server a message comprising the set of the encrypted ID and the public key stored in the device; and detecting whether the message is directed toward a data store for the tenant by comparing the set comprised in the message and the set stored in the server.

6 Claims, 7 Drawing Sheets

PRIOR ART

SECURE MESSAGE ROUTING IN MULTI-TENANT SYSTEM WITHOUT CONTENT INSPECTION

BACKGROUND

The present invention generally relates to a method for secure message routing in a multi-tenant system.

Being able to securely send messages to a shared infrastructure such as a multi-tenant cloud or a multi-tenant datacenter is critical to realizing the cost advantages of shared computer infrastructures. However, routing messages through shared data entry points normally requires some examination of the message contents to verify correct customer data routing.

Generally, a simple network address or a customer name or ID such as a customer seed ID is used to route the message correctly. However, the manipulation of the customer ID may cause a legal risk in many industries. For example, in the healthcare industry, routing confidential patient information to a wrong provider or hospital may lead to fines, penalties, and patient risks. In industries that fall under anti-trust laws, maintaining any information from competitors can lead to anti-trust violations and fines.

One possible solution to avoid such legal risks discussed above is to utilize encryption throughout the message transmission through the shared cloud or datacenter infrastructure. However, there still is a risk that the encryption keys themselves are compromised and utilized to send the message to a wrong customer or even route it to an attacker. Such a solution for message encryption in the shared cloud and datacenter computer infrastructure relies on block cyphers or symmetric cryptography, i.e., the key for encrypting the message is the same one utilized to decrypt the message, because the symmetric encryption is far less computationally intensive than other encryption methods such as public key/private key encryption.

SUMMARY

One or more embodiments of the invention provide a method for message routing in a multi-tenant system, comprising: encrypting an ID of a tenant with a public key that is generated for the tenant together with a corresponding private key; storing a set of the encrypted ID and the public key in both a device and a server of the multi-tenant system; transmitting from the device to the server a message comprising the set of the encrypted ID and the public key stored in the device; and detecting whether the message is directed toward a data store for the tenant by comparing the set comprised in the message and the set stored in the server.

One or more embodiments of the invention provide a system comprising: a server that comprises a data store; a first device that transmits a message to the server; and a second device that: encrypts an ID of a tenant with a public key that is generated for the tenant together with a corresponding private key; and stores a set of the encrypted ID and the public key in both the server and the first device, wherein the first device transmits to the server the message comprising the set of the encrypted ID and the public key; and the server detects whether the message is directed toward the data store for the tenant by comparing the set comprised in the message and the set stored in the server.

Other aspects of the invention will be apparent from the following description and the appended claims.

DETAILED DESCRIPTION

Figure 1:
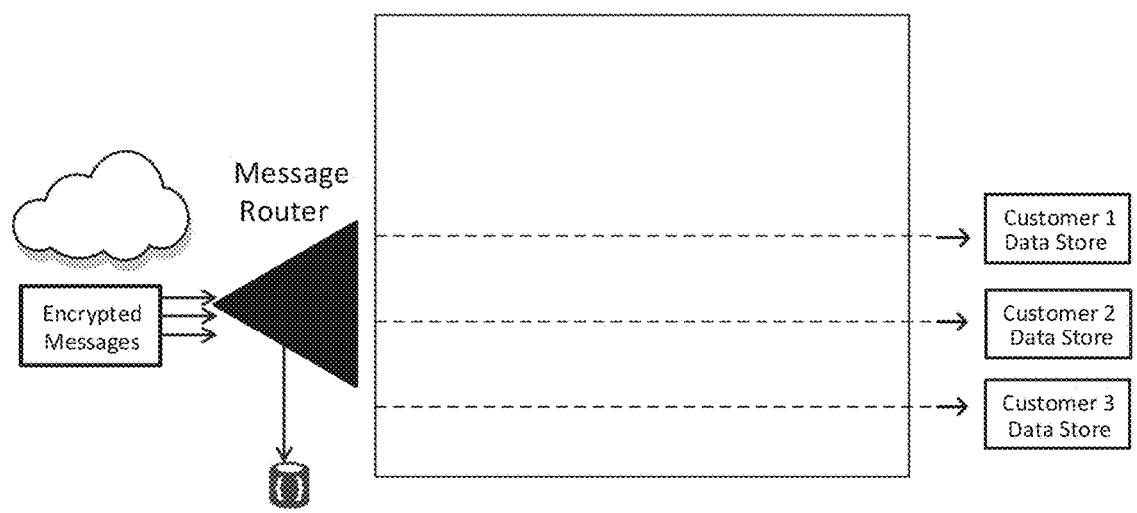
FIG. 1 shows a schematic view of a conventional message routing scheme in a multi-tenant system.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

FIG. 1 shows a conventional multi-tenant system such as a multi-tenant cloud or a multi-tenant datacenter that comprises a message router, which receives messages from tenant's or customer's devices via the Internet. The message router has a function for decrypting those messages to identify the customers and to correctly route and store each of the messages onto a correct customer's data store. In other words, encryption is broken by such routing function to achieve correct delivery to the data store. Thus, there is a risk that the customer ID required for message routing is spoofed or forged through the routing process. Thus, each customer needs to implicitly trust the security of the routing function to correctly route messages not only for their company, but also, for all others using the shared cloud or datacenter infrastructure.

One or more embodiments of the invention is directed toward a method and a system that eliminate the aforementioned risks of the conventional message routing in the multi-tenant system. In one or more embodiments of the invention, a public key encryption scheme is used to correctly route a customer message to a correct data store without intermediate decryption and inspection of the message content. To achieve this, each customer prepares at least: (i) intermediate data (pre-calculated data), which is a customer ID encrypted by a public key for the customer, and (ii) a receiver module, which is implemented on a server and is responsible for verifying a message including the pre-calculated data (i.e., encrypted customer ID) with the private key and for storing the message content onto the customer data store. The pre-calculated data is stored on both a customer device(s) and the server as part of the receiver module in advance.

After the pre-calculation process, the customer device transmits a message including the pre-calculated data, as well as business data, to be stored in the customer data store on the server. Once the message is received by the server, the message is forwarded to receiver modules prepared by several customers. Each of the receiver modules then determine whether the message is directed toward the receiver module, by comparing the pre-calculated data included in the message and the one stored in advance. If the message is directed toward the receiver module, the receiver module decrypts and stores the message content onto the data store. On the other hand, if the message is not directed toward the receiver module, i.e., the pre-calculated data included in the message and the one stored in the receiver module are inconsistent, the receiver module discards the message. In that case, the receiver module cannot decrypt the message and access the customer ID because the private key of the receiver module cannot be used to decrypt the other customer's pre-calculated data.

As a result, the decryption and inspection of the message contents in the routing process may be avoided, which eliminates the possibility that the message is compromised and sensitive data is routed in a malicious manner (e.g. a competitors data being routed to prompt an anti-trust fine). Moreover, sharing the pre-calculated data in advance can prevent the processing load from increasing in spite of using the public/private key encryption scheme, which is generally known as requiring many computer resources.

Figure 2:
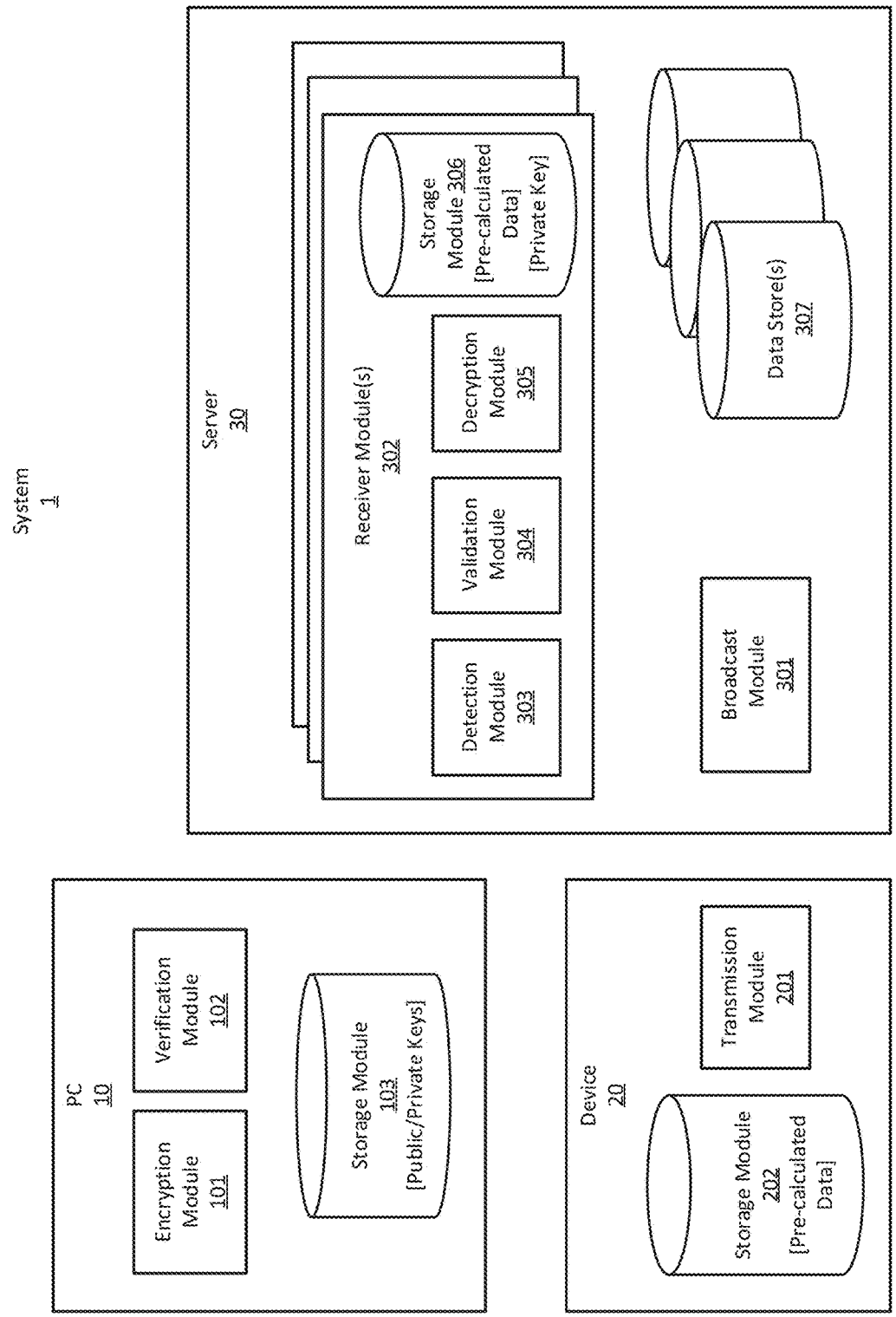
FIG. 2 shows a block diagram of a system in accordance with one or more embodiments of the invention.

FIG. 2 shows a block diagram of a system 1 in accordance with one or more embodiments of the invention. The system 1 comprises: a PC 10 that generates the pre-calculated data for a customer; a device 20 that transmits an encrypted message including the pre-calculated data and a specific message to be stored on the customer's data store; and a server 30 that handles and stores messages from several customers onto correct data stores via the message module prepared by each customer.

The PC 10 comprises an encryption module 101, a verification module 102, and a storage module 103, and generates the pre-calculated data that is required in subsequent message transmission and routing process based on a customer ID and a key pair. For example, the ID is a customer seed ID (e.g. 12345) and the key pair is a pair of a public key and a private key for the receiver module of the customer. The customer ID may be determined by the customer, and the key pair may be generated by any commercially available certificate authority (e.g. the OpenCA certificate server).

Figure 3:
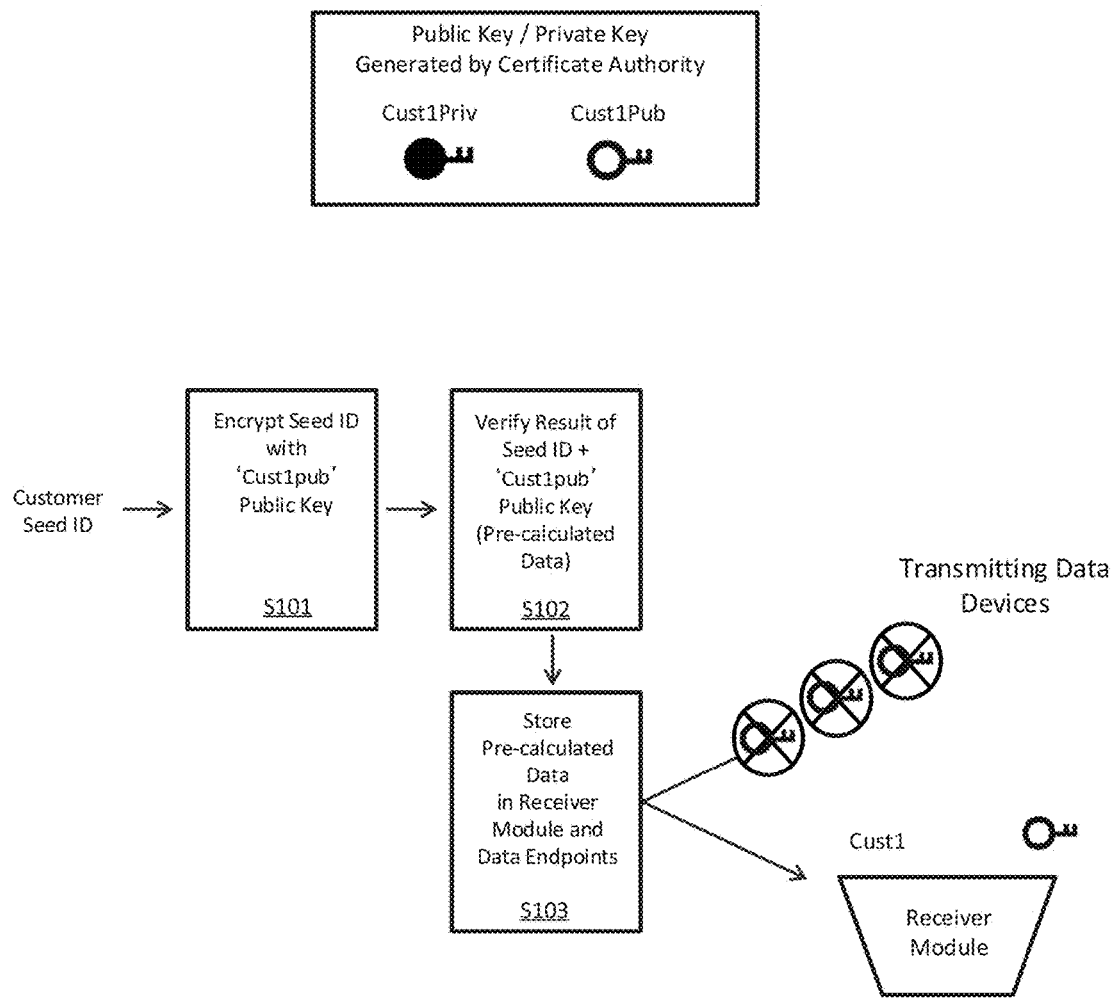
FIG. 3 shows a flow of the process performed by the system in accordance with one or more embodiments of the invention.

FIG. 3 shows a flow of the process performed by the system 1 in accordance with one or more embodiments of the invention. The process for generating the pre-calculated data in the PC 10 is described in FIG. 3. It is assumed that a public/private key pair ("Cust1Pub" and "Cust1Priv") has been generated for a customer and is stored in the storage module 103 of the PC 10.

First, the encryption module 101 of the PC 10 encrypts the customer seed ID with the public key (S101), and stores the result (the customer seed ID and the public key "Cust1Pub") in the storage module 103 as the pre-calculated data. Next, the verification module 102 verifies that the pre-calculated data can be decrypted with the corresponding private key "Cust1Priv" and the customer seed ID is yielded correctly (S102). Once the pre-calculated data is verified, the verification module 102 stores the pre-calculate data onto the device 20 and the server 30 (the receiver module for the customer) (S103). As a result, the device 20 may transmit a message with the pre-calculated data, and the receiver module for the customer operating in the server 30, which also has the private key, may verify the encrypted customer seed ID and store the message content onto a data store correctly.

In one or more embodiments of the invention, the storage module 103 of the PC 10 may store the customer seed ID. Additionally, the storage module 103 may further store a data endpoint ID (or a device ID), which identifies the device 20 and is used for transmitting the message to the server 30. The data endpoint ID may be determined and input to the PC 10 by the customer.

Referring back to FIG. 2, the device 20 comprises a transmission module 201 and a storage module 202 and transmits to the server 30 a message, which contains some business data to be stored on the data store in the server 30, with the pre-calculated data received from the PC 10. In one or more embodiments of the invention, two or more devices 20 are used for transmitting the message containing the data to be stored on the customer's data store. Each device 20 has a data endpoint ID to identify the origin of the message transmitted to the server 30. The data endpoint ID may be pre-configured to each device 20 or remotely configured via the PC 10 as discussed above.

Figure 4:
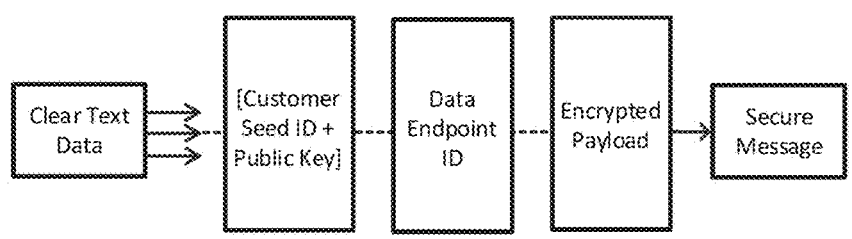
FIGS. 4, 5, and 6A-6C each show an implementation example of an encrypt message in accordance with one or more embodiments of the invention.
Figure 5:
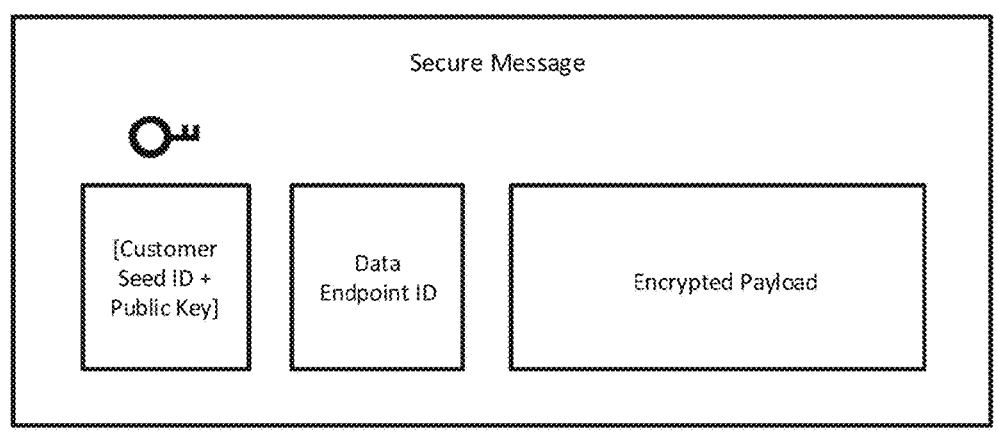

FIG. 4 and FIG. 5 each show an example of assembling a secure message in the device 20.

As shown in FIG. 4, once some event occurs for transmitting data to the server 30, the transmission module 201 of the device 20 assembles a secure message (an encrypted message) in the following order: (i) the customer seed ID plus the public key (i.e., the pre-calculated data); (ii) the data endpoint ID assigned to the device 20; and (iii) an encrypted payload, which is originated from input clear text data indicating the data to be transmitted and stored in the data store for the customer. In one or more embodiments of the invention, the payload is encrypted by a block cipher associated with the customer. FIG. 5 shows a block diagram of an assembled secure message including the above elements (i)-(iii).

Figure 6A:
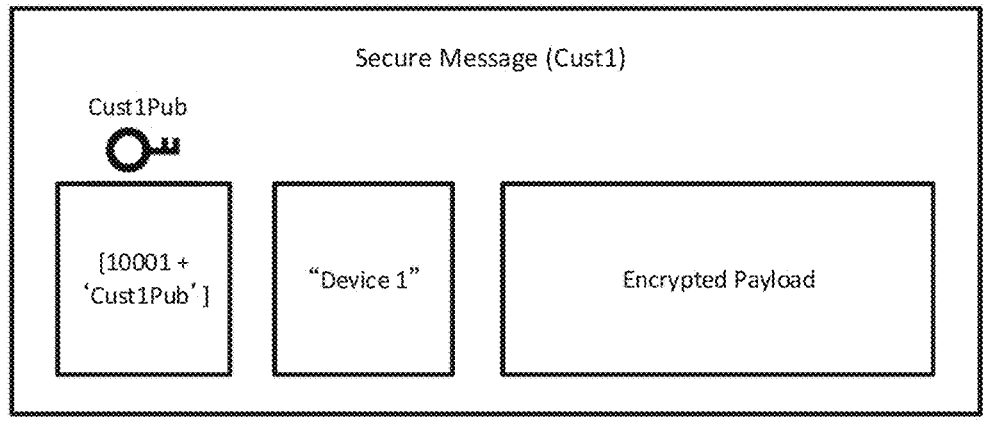
Figure 6B:
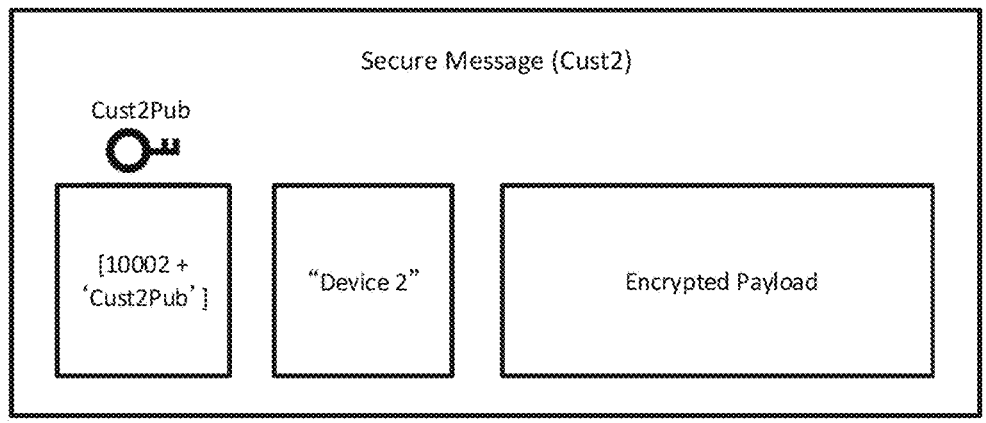
Figure 6C:
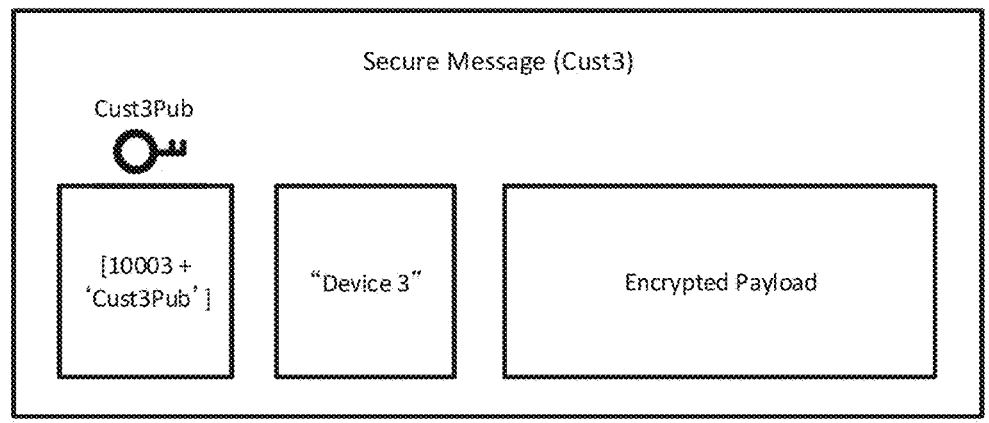

FIGS. 6A-6C each show an example of an assembled secure message for three customers "Cust1," "Cust2," and "Cust3," each having the customer seed ID "10001," "10002," and "10003." As shown in FIGS. 6A-6C, the secure message for each customer comprises: (i) the pre-calculated data (i.e., the customer seed ID encrypted by the public key for each customer); (ii) the data endpoint ID of the device 20 assembling and transmitting this secure message; and (iii) the encrypted payload indicating the data to be stored in the customer's data store. Once assembling the secure message, the transmission module 201 of the device 20 transmits it to the server 30 via a network such as the Internet.

Referring back to FIG. 2, the server 30 comprises a broadcast module 301, a receiver module 302, and a data store 307. In one or more embodiments of the invention, two or more receiver modules 302 and data stores 307 are installed for two or more customers. The receiver module 302 is prepared by each customer and comprises a detection module 303, a validation module 304, a decryption module 305, and a storage module 306 storing the pre-calculated data and the private key of the customer. The receiver module 302 may receive the secure message and store the data onto the data store 307, which is associated with the customer.

Figure 7:
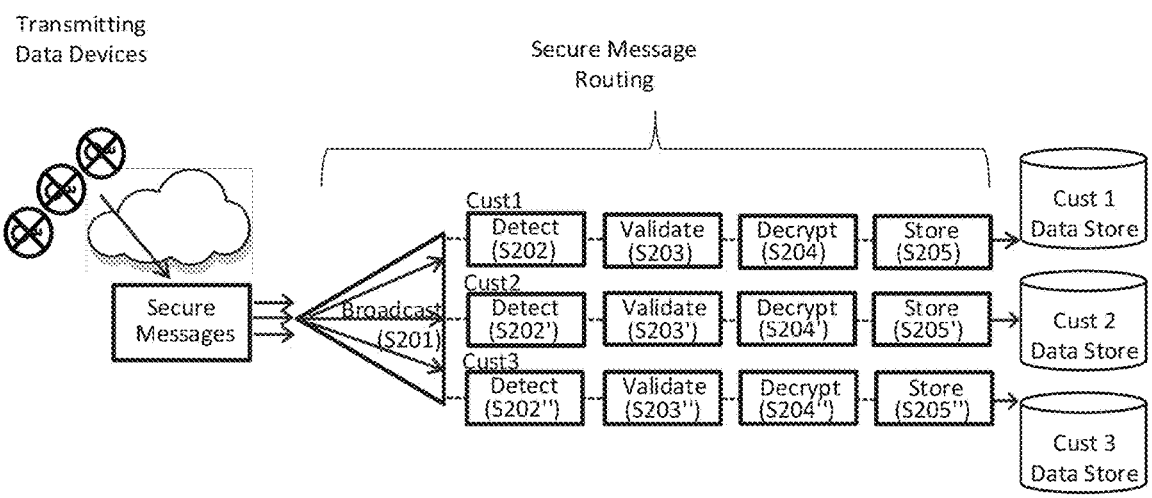
FIGS. 7-8 each show a flow of the process performed by the system in accordance with one or more embodiments of the invention.
Figure 8:
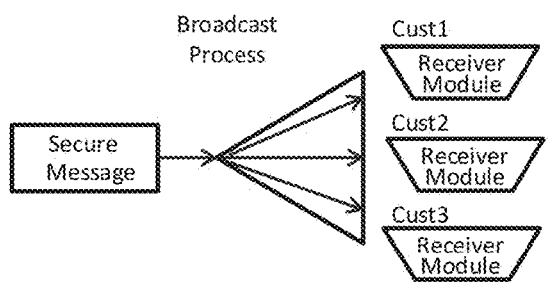

FIG. 7 and FIG. 8 each show a flow of the process performed by the system 1 in accordance with one or more embodiments of the invention. It is assumed that three receiver modules 302 are installed for three customers Cust1, Cust2, and Cust3, and each of them stores the private key for the customer.

As shown in FIG. 7, the server 30 receives several secure messages assembled and transmitted by the devices 20 for the different customers as shown in FIG. 6. When the server receives one of the secure messages, the broadcast module

301 broadcasts the message to all of the receiver modules 302 installed on the server 30 (S201).

FIG. 8 illustrates the broadcast process of a single secure message toward three receiver modules prepared by different customers. In one or more embodiments of the invention, such broadcasting may be done via span port forwarding that mirrors all traffic to all network device ports.

Next, the detection module 303 of each receiver module 302 detects whether the message is addressed toward itself by comparing the pre-calculated data (i.e., encrypted customer seed ID) included in the received message and the one stored in the storage module 306 (S202). The detection module 303 may determine that the message is addressed toward itself when both pre-calculated data are consistent.

When the detection module 303 detects that the message is addressed toward the receiver module 302, the validation module 304 validates the origin of the received message by reading the second field of the secure message (i.e., "Data Endpoint ID" field of FIG. 5) (S203). Subsequently, the decryption module 305 decrypts the payload of the message with the block cipher associated with the customer (S204) and stores the data onto the data store 307 (S205). In one or more embodiments of the invention, the data may be stored based on the data endpoint ID.

According to one or more embodiments of the invention, the message routing process in the server may be secure and quick because no decryption operation is involved in the receiver modules to which the secure message is not directed. In other words, there is no chance that the encrypted customer seed ID is compromised by some intermediary in the routing process. Moreover, simplifying the initial routing process of the message with the broadcast process allows the server 30 to be free from logic interpretation. Furthermore, because the device 20 transmitting data and the receiver module 302 on the server 30 share the customer seed ID encrypted by the public key (i.e., pre-calculated data), the receiver module 302 may detect a message directed toward itself without recalculation by the private key every time when receiving messages.

Figure 9:
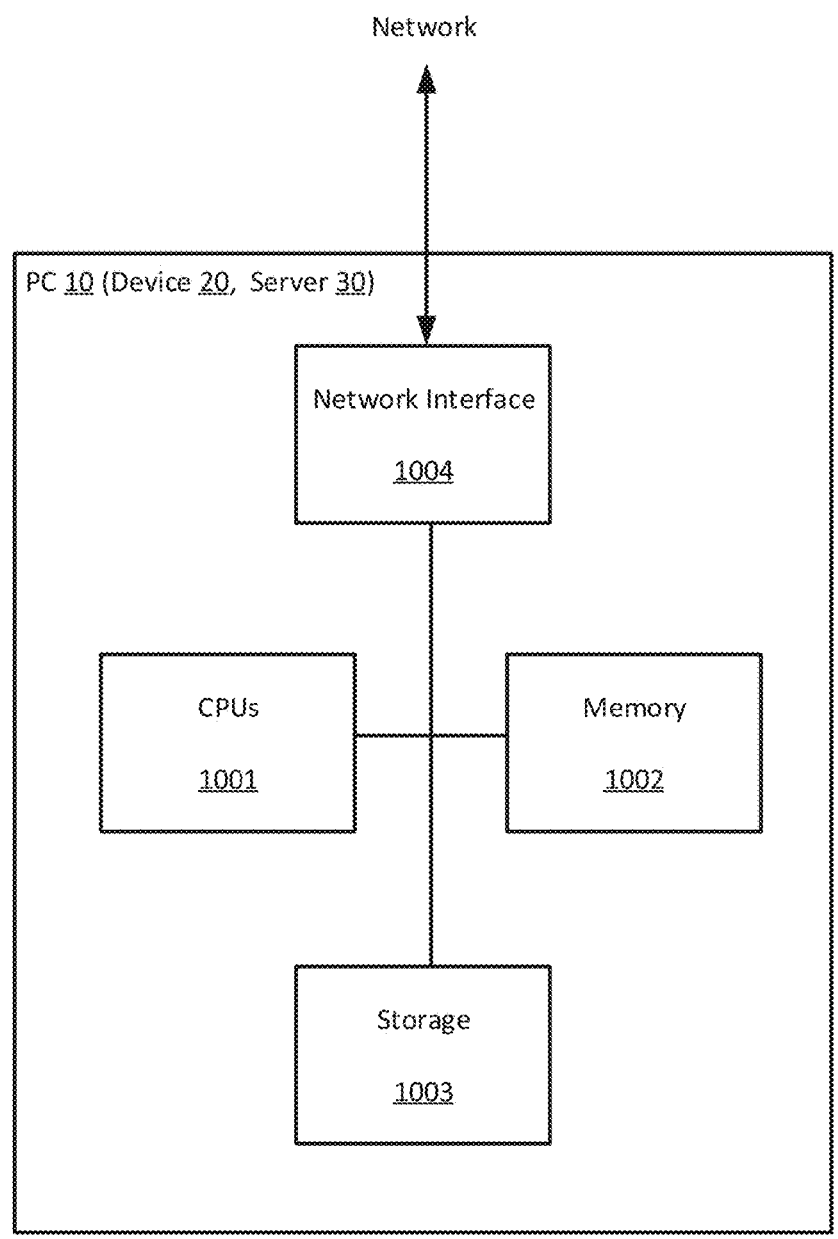
FIG. 9 shows an implementation example of a PC, a device, and a server in accordance with one or more embodiments of the invention.

FIG. 9 shows an implementation example of the PC 10, the device 20, and the server 30 in accordance with one or more embodiments of the invention.

In one or more embodiments of the invention, the PC 10, the device 20, and the server 30 may each comprise one or more CPUs 1001, a memory 1002 associated with the CPUs 1001, a storage 1003, and a network interface 1004 that communicates with another device via a network such as the Internet. The PC 10, the device 20, and the server 30 may each comprise any other hardware components not shown in FIG. 9. Each of the PC 10, the device 20, and the server 30 may operate under a different computer architecture. A network storage may be used instead of the storage 1003.

In one or more embodiments of the invention, the modules shown in FIG. 2 may be implemented by software or hardware or combination thereof. For example, each of the modules is a program executed by the CPUs 1001. Alternatively, some or all of the modules may be implemented by dedicated hardware such as a controller or a circuit.

In one or more embodiments of the invention, the server 30 is a multi-tenant cloud or a multi-tenant datacenter, which operates as a cloud-based computer system. In that case, the components shown in FIG. 9 may be distributed over multiple computers via networks. For example, the storage 1003 may be implemented in another hardware accessible over the network via the network interface 1004.

As discussed above, one or more embodiments of the invention assure end-to-end message security by mandating message confidentiality through encryption that does not need to be decrypted by intermediate processes (e.g. simple routing functions). Additionally, spoofing and forging of the customer ID, such as customer seed ID, are minimized to only affect one customer not the entire infrastructure. Furthermore, malicious routing of messages to wrong customers is prevented and can easily be detected.

In one or more embodiments of the invention, the concept of the pre-calculation of a customer seed ID and a public key may be extended to the devices 20 that transmit data to the server 30. In that case, a certain number of key pairs (i.e., a public and a private key) are generated for all of the devices 20, and the data endpoint ID of each device 20 is encrypted by its public key like the customer seed ID leading to "pre-calculated data" discussed above. The encrypted data endpoint IDs are stored in each device 20 and the server 30 (e.g., the storage module 306 of the receiver module 302), and the device 20 may transmit a secure message including the encrypted data endpoint ID so that the receiver module 302 may verify the endpoint data source of all data.

In one or more embodiments of the invention, the pre-calculation may be superimposed with an ultra customer seed ID with public keyed results for enciphering the actual end data store results that then could only be decrypted by special customer held only keys in a zero trust model. This would provide the ultimate in data confidentiality in that the actual data would only be read out from the cloud data store with an appropriate ultra customer private key.

In one or more embodiments of the invention, the device 20 (i.e., data endpoint) has its own data endpoint private key. Since typical data transmitted from the device 20 to the server 30 may include generic values of 1 for "On" and 0 for "Off," these values can be pre-calculated with private keys of the end points themselves. It may provide block cypher computational performance with private key assurance of data origin.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for message routing in a multi-tenant system, comprising:
    encrypting an ID of a tenant with a public key that is generated for the tenant together with a corresponding private key;
    storing a set of the encrypted ID and the public key in both a device and a server of the multi-tenant system;
    transmitting from the device to the server a message comprising the set of the encrypted ID and the public key stored in the device;
    detecting by each of a plurality of receivers that are within the server whether the message is directed toward a data store for the tenant by comparing the set comprised in the message and the set stored in the server; and
    storing, by one of the plurality of the receivers, a payload of the message onto the data store associated with the one of the plurality of receivers based on the comparison.

2. The method of claim 1, wherein
    the payload is encrypted by a block cypher associated with the tenant, and the method further comprises decrypting, by the one of the plurality of receivers, the encrypted payload with a block cipher.

3. The method of claim 2, wherein the message comprises a data endpoint ID that identifies the device that has sent the message to the server, and the method further comprises storing the decrypted payload based on the data endpoint ID.

4. A system comprising:

a server that comprises a data store and a plurality of receivers;

a first device that transmits a message to the server; and a second device that:
  encrypts an ID of a tenant with a public key that is generated for the tenant together with a corresponding private key; and
  stores a set of the encrypted ID and the public key in both the server and the first device, wherein the first device transmits to the server the message comprising the set of the encrypted ID and the public key, each of the plurality of receivers detects whether the message is directed toward the data store for the tenant by comparing the set comprised in the message and the set stored in the server, and one of the plurality of receivers stores a payload of the message onto the data store associated with the one of the plurality of the receivers based on the comparison.

5. The system of claim 4, wherein the payload is encrypted by a block cypher associated with the tenant, and the one of the plurality of receivers decrypts the encrypted payload with a block cipher.

6. The method of claim 5, wherein the message comprises a data endpoint ID that identifies the device that has sent the message to the server, and the one of the plurality of receivers stores the decrypted payload based on the data endpoint ID.

* * * * *